US010149646B1

(12) United States Patent
Andreadis

(10) Patent No.: US 10,149,646 B1
(45) Date of Patent: Dec. 11, 2018

(54) SYSTEM AND METHOD FOR OBJECTIVELY EVALUATING SHOULDER JOINT STABILITY

(71) Applicant: Elizabeth Andreadis, Mesa, AZ (US)

(72) Inventor: Elizabeth Andreadis, Mesa, AZ (US)

( * ) Notice: Subject to any disclaimer, the term of this patent is extended or adjusted under 35 U.S.C. 154(b) by 0 days.

(21) Appl. No.: 15/621,740

(22) Filed: Jun. 13, 2017

(51) Int. Cl.
| A63B 24/00 | (2006.01) |
| A63B 22/14 | (2006.01) |
| A61B 5/00 | (2006.01) |
| A61B 5/11 | (2006.01) |
| G01P 15/18 | (2013.01) |

(52) U.S. Cl.
CPC .......... *A61B 5/4576* (2013.01); *A61B 5/0051* (2013.01); *A61B 5/1121* (2013.01); *A61B 5/4528* (2013.01); *G01P 15/18* (2013.01); *A61B 5/002* (2013.01); *A61B 5/0022* (2013.01); *A61B 5/7271* (2013.01); *A61B 5/742* (2013.01); *A61B 2562/0219* (2013.01)

(58) Field of Classification Search
CPC ............................ A61B 5/4576; A61B 5/0051
See application file for complete search history.

(56) References Cited

U.S. PATENT DOCUMENTS

| 2,523,547 | A | 9/1950 | Zerkle |
| 5,871,423 | A | 2/1999 | Pruchnik |
| 6,039,679 | A | 3/2000 | Yu |
| 6,846,270 | B1 * | 1/2005 | Etnyre ................ A63B 21/00 428/8 |
| 7,615,018 | B2 | 11/2009 | Nelson et al. |
| 9,028,378 | B2 | 5/2015 | Shah |
| 9,408,774 | B2 | 8/2016 | Rafaeli |
| 2001/0000782 | A1 * | 5/2001 | Schiessl ................ A61H 1/003 482/146 |
| 2013/0210577 | A1 * | 8/2013 | Ceoldo ................ A61H 7/001 482/1 |
| 2013/0218058 | A1 | 8/2013 | Ceoldo et al. |

FOREIGN PATENT DOCUMENTS

WO     WO 2013040424 A1 *  3/2013  ............... A61B 5/11

* cited by examiner

*Primary Examiner* — Sean Dougherty
*Assistant Examiner* — Nicholas E Kolderman
(74) *Attorney, Agent, or Firm* — Morgan Law Offices, PLC

(57) ABSTRACT

The present disclosure relates to objective evaluation of shoulder stability. An accelerometer is attached adjacent the subject's shoulder and the subject is provided with a vibrating device that is held in the hand of the subject's outstretched arm. The subject is instructed to keep his or her arm as still as possible while holding the vibrating device. Data is obtained from the accelerometer over a predetermined length of time. Using a processor, preferably wirelessly connected to the accelerometer, shoulder stability is evaluated in relation to the subject's ability to resist vibratory forces. In an embodiment, the processor evaluates shoulder stability by averaging measured g-forces obtained from the accelerometer along three axes. The average g-forces across each axis are averaged together to give an overall average. The overall average is compared with available normative values to determine the risk level.

10 Claims, 4 Drawing Sheets

SYSTEM AND METHOD FOR OBJECTIVELY EVALUATING SHOULDER JOINT STABILITY

BACKGROUND OF THE INVENTION

1. Field of the Invention

The present invention relates to a system and method for objectively evaluating shoulder joint stability.

2. Description of the Related Art

FIG. 1 illustrates the anatomy of the human shoulder 50. As shown, the human shoulder 50 connects the clavicle (collar bone) 10, scapula (shoulder blade) 20, and humerus 30 (upper arm). Although not depicted, it is to be understood that the shoulder further includes various associated muscles, ligaments and tendons. Further, the area around the clavicle 10, scapula 20, and humerus 30 includes a ball and socket joint known as the glenohumeral joint or shoulder joint, which is the main joint of the shoulder. The shoulder joint permits the arm to rotate or to move outwardly and vertically from the body.

Unfortunately, various ailments stemming from injury, overuse and natural aging as well as neurological disorders can cause shoulder instability. A person with normal shoulder stability is able to control movement of his or her arm as it is extended, rotated, and held upwardly and downwardly. Conversely, a person with poor shoulder stability will have difficulty controlling normal shoulder motion particularly against a resistive force, and may, for example, not be able to keep his or her arm still while extended for an appreciable amount of time, particularly while holding an object.

Conventionally, shoulder ailments are investigated using physical examination. However, current medical practices utilized to evaluate shoulder stability are subjective and limited by the examiner's level of experience and technical expertise. Shoulder stability tests are usually performed during the initial evaluation process and request subject feedback. These tests have low inter-rater reliability and have no normative measures aside from the subject's feedback. Even magnetic resonance imaging (MRI) and computed tomography (CT) only provide a static picture of the soft tissue. They can assess structural integrity, but do not measure stress on those structures. Currently there is no way for a clinician to obtain objective data on a subject regarding the subject's shoulder stability.

SUMMARY OF THE INVENTION

The present disclosure relates to objective evaluation of shoulder stability. An accelerometer is attached adjacent the subject's shoulder and the subject is provided with a vibrating device that is held in the hand of the subject's outstretched arm. The subject is instructed to keep his or her arm as still as possible while holding the vibrating device. Data is obtained from the accelerometer over a predetermined length of time. Using a processor, preferably wirelessly connected to the accelerometer, shoulder stability is evaluated in relation to the subject's ability to resist vibratory forces. In an embodiment, the processor evaluates shoulder stability by averaging measured g-forces obtained from the accelerometer along three axes. The average g-forces across each axis are averaged together to give an overall average. The overall average is compared with available normative values to classify the subject's risk level.

DETAILED DESCRIPTION OF THE INVENTION

Figure 1:
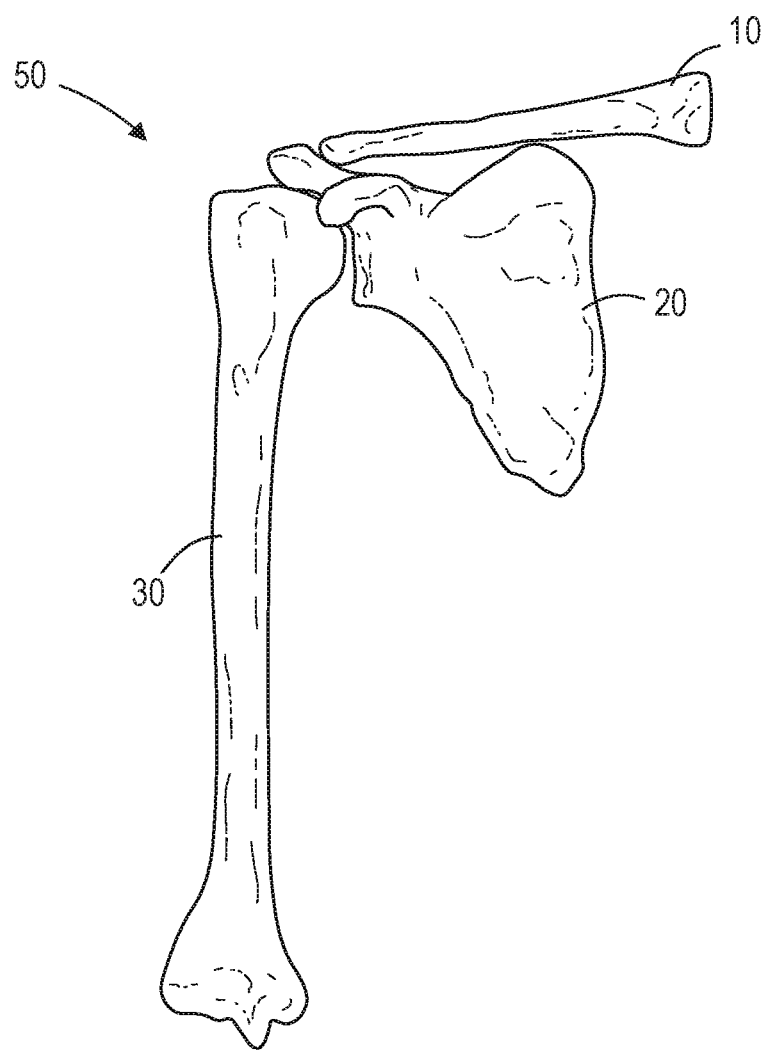
FIG. 1 illustrates an anatomy of the human shoulder.
Figure 2:
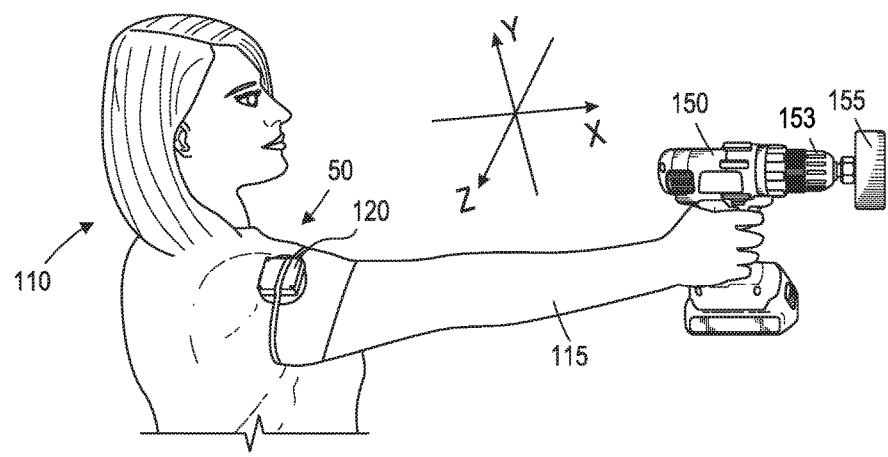
FIG. 2 illustrates a subject being evaluated for shoulder stability, according to an exemplary embodiment.

Referring to FIG. 2, a subject 110 being evaluated for shoulder stability, according to an exemplary embodiment, is illustrated. The subject 110 is fitted with an accelerometer 120 strapped to the subject's shoulder area 50. The accelerometer 120 is a three-axis accelerometer. The accelerometer 120 measures acceleration forces in terms of g-forces along each of the three axes, x, y and z, of three-dimensional space. The subject 110 is instructed to hold a vibrating device 150 in his or her hand while the arm 115 of the subject 110 is outstretched, as shown. The subject is instructed to keep his or her arm as still as possible while holding the vibrating device 150. Joint stability relates to the body's ability to counteract external physical forces. In general, the stronger the stabilizing muscles are, the better they can counteract external forces, such as the forces from the vibrating device 150 which will result in less g-forces measured by the accelerometer 120 along each axis.

Figure 3:
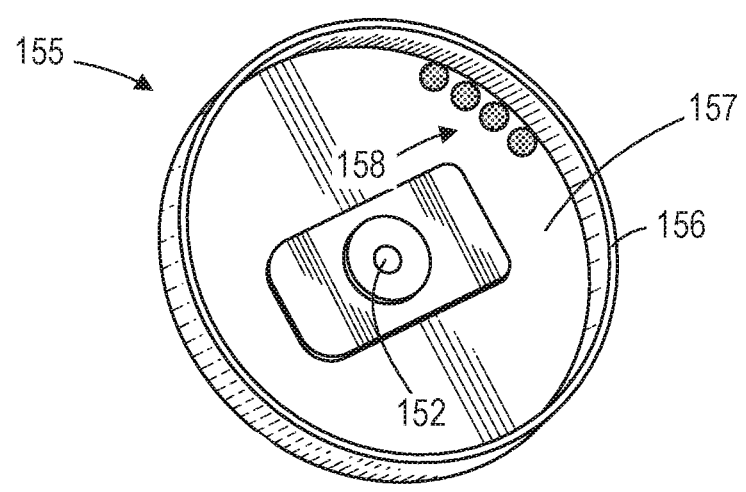
FIG. 3 illustrates an underside of a rotatable attachment having an offset mass.

As shown in FIG. 2, the vibrating device 150 is a hand-held motorized device such as a battery-powered electric drill 150 with a vibrating disc 155 attached to the chuck 153 of the drill 150. Once the test is about to start, the subject 110 is instructed to activate the vibrating device 150 by pressing the trigger or the like. As illustrated in FIG. 3, the vibrating disc 155 includes a circular perimeter 156 with a center 152. In an interior portion 157 of the disc 155, offset weights 158 are attached near the perimeter 156 creating an uneven distribution of mass around the center 152. Accordingly, as the disc 155 is rotated, the uneven distribution of mass will cause the disc 155 to vibrate. In an embodiment, the vibrating disc 155 rotates at about 650 rpm, the offset weight 158 weighs about 4 oz. and is disposed about 2 inches from the center 152. It is to be understood that the illustrated vibrating device 150 is shown for illustrative purposes and that many other such hand-held vibrating devices could instead be used to produce sufficient vibration. Furthermore, it is to be understood that rather than the subject 110 starting the vibrating device 150, this may be done remotely or otherwise.

Figure 4:
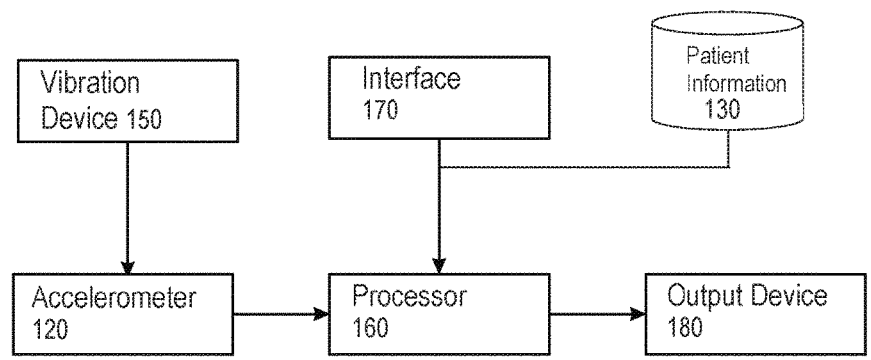
FIG. 4 illustrates a block diagram of a system for evaluating shoulder stability, according to an exemplary embodiment.

Referring to FIG. 4, an exemplary system for objectively evaluating joint stability 100 is illustrated. The system for objectively evaluating joint stability 100 includes the accelerometer 120, the vibrating device 150, a processor 160, an interface 170, and an output device 180. The accelerometer 120 can be wirelessly connected to the processor 160 using a suitable short distance communication protocol such as Bluetooth™ or the like, a local area network (LAN), an Intranet or the Internet, etc. In other embodiments, the accelerometer 120 is wired to the processor. In certain embodiments, the accelerometer 120 and the processor 160 are housed together. The processor 120 can be a computer system, such as a personal computer (desktop, laptop, tablet) or a server. In some embodiments, the processor includes a cloud-based server. In still other embodiments, the processor 120 will be a programmable microcontroller, an application-specific integrated circuit (ASIC), or a hard-wired circuit. Preferably, the processor 160 will be a programmable processor capable of using data obtained from the accelerometer 120 to evaluate joint stability of the subject 110 in the manner disclosed herein.

In operation, the processor 160 will obtain patient information 130 from a database or other file system for the subject 110. Such information can include medical record information including results from previous joint stability tests. Using the interface 170, the processor 160 can prompt the clinician for the type of test being conducted, and the clinician can enter or select the type of test and other information for the subject, such as whether the right or left shoulder is being evaluated. The processor 160 will start a timer once either the clinician indicates the test has started (or the timing may be indicated by the clinician).

The manner in which the processor 160 will be instructed to operate (e.g., programmed) will depend on the particular accelerometer hardware and operating system being used. In many implementations, the accelerometer 120 returns multi-dimensional arrays of sampled sensor values. Typically, the arrays will be structured for acceleration values along the three axes, and expressed in $m/s^2$ units of measure. As mentioned, joint stability relates to the body's ability to counteract external physical forces. In general, the stronger the stabilizing muscles are, the better they can counteract external forces, such as the vibratory forces from the vibrating device 150 which will result in less g-forces measured by the accelerometer 120 along each axis. In an embodiment, the processor 160 calculates an average g-force value across each of the axes. A higher average indicates greater movement from the origin O along the particular axis. The amount of displacement is an indication of how much the humerus moved during the testing period along the given axis. An important therapeutic goal is to have as small an average as possible. The average g-forces across each axis can be averaged together to give an overall average. The overall average can be compared with available normative values. The risk level can be assessed as "low," "moderate," or "high" risk, for example. In an embodiment, these labels are dependent on the standard deviations away from normal. It is to be understood that the term "average" can include various types of averages (e.g., arithmetic mean, median, truncated mean, weighted mean, winsorized mean) and, in various embodiments, other measures of central tendency can be used.

In an embodiment, the processor can utilize other factors such as the age/gender of the subject 110, along with predetermined guidelines, to more properly assess the subject 110. An evaluation report can be outputted via the output device 180, which can include summary and detailed information, as well as longitudinal information including previous evaluations. The output device 180 can include a display device and/or a printer.

The following example of how the test is performed by a clinician is provided for illustrative purposes.

An explanation of the test is provided to the subject 110. The accelerometer 120 is secured just below the greater tubercle of the humerus and then secured again with an elastic wrap. The subject 110 is shown a demonstration of each position to be assumed. The arm of the subject 110 is held out directly in front (at 90 degrees shoulder flexion) with the elbow locked out straight. The subject 110 is told to pull his or her shoulder back as if trying to draw it into the shoulder joint of the subject 110. The subject 110 is provided with the vibrating device 150 which is held in the hand of the subject 110. It is explained to the subject that they will need to hold the device in the correct position for 10 seconds. When ready and comfortable, the subject 110 squeezes the trigger of the vibrating device 150, and data collection begins. The subject 110 is given prompts as to how much time is remaining. Once data collection is finished, the subject 110 is told to relax.

While this invention has been described in conjunction with the various exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A method of evaluating shoulder joint stability, comprising:
    equipping a subject with an accelerometer attached adjacent to the subject's shoulder joint and a vibrating device held in the hand of the subject's outstretched arm;
    instructing the subject to keep the subject's outstretched arm still while holding the vibrating device during a predetermined length of time;
    receiving motion data from the accelerometer over the predetermined length of time, the motion data received from the accelerometer including measured movements of the subject's shoulder joint in terms of g-forces along each of three axes;
    using a processor to evaluate shoulder joint stability of the subject's shoulder joint at least in part by calculating averages of each of the measured g-forces along the three axes, and using the calculated averages in comparison with predetermined normative values to determine the subject's joint stability risk level; and
    using an output device to output information regarding the determined subject's shoulder stability joint risk level.

2. The method of claim 1, wherein the evaluation by the processor is further based in part on input patient information.

3. The method of claim 1, wherein the accelerometer wirelessly communicates with the processor.

4. A system for evaluating shoulder joint stability, comprising:
    a vibrating device held in the hand of an outstretched arm of a human subject for a predetermined length of time;
    an accelerometer attached adjacent to the shoulder joint of the outstretched arm;
    a processor, in communication with the accelerometer; and
    an output device;
    wherein the processor is configured to receive motion data obtained from the accelerometer to evaluate shoulder joint stability of the subject's shoulder joint;
    wherein the motion data received from the accelerometer includes measured movements of the subject's shoulder joint in terms of g-forces along each of three axes;
    wherein the processor evaluates shoulder stability of the subject's shoulder joint at least in part by calculating averages of each of the measured g-forces along the three axes, and using the calculated averages in comparison with predetermined normative values to determine the subject's joint stability risk level; and wherein the output device outputs information regarding the determined subject's shoulder joint stability risk level.

5. The system of claim 4, wherein the vibrating device includes an electric motor that drives a rotating shaft, the rotating shaft having a rotating disc attached thereto with an uneven distribution of mass around its center.

6. The system of claim 4, wherein the evaluation is further based in part on input patient information.

7. The system of claim 4, wherein the evaluation is further based in part on guidelines.

8. The system of claim 4, wherein the evaluation is further based on previous evaluations of the subject over time.

9. The system of claim 4, wherein the accelerometer wirelessly communicates with the processor.

10. The system of claim 4, wherein the processor is configured to average together the calculated averages to give an overall average, the overall average compared with the normative values to classify the subject's joint stability risk level.

\* \* \* \* \*